United States Patent [19]

Imagawa et al.

[11] Patent Number: 5,450,200
[45] Date of Patent: Sep. 12, 1995

[54] METHOD OF AND APPARATUS FOR MEASURING BIREFRINGENCE

[75] Inventors: Kyouji Imagawa, Takarazuka; Kiyokazu Sakai, Nishinomiya, both of Japan

[73] Assignee: New Oji Paper Co., Ltd., Tokyo, Japan

[21] Appl. No.: 216,457

[22] Filed: Mar. 23, 1994

[30] Foreign Application Priority Data

Mar. 31, 1993 [JP] Japan .................................. 5-074575
May 31, 1993 [JP] Japan .................................. 5-129588

[51] Int. Cl.⁶ .......................... G01J 4/00; G01B 11/18
[52] U.S. Cl. ........................... 356/364; 356/35; 356/367; 250/225
[58] Field of Search ............... 356/364, 365, 366, 367, 356/368, 369, 370, 128, 351, 32–35.5; 250/225

[56] References Cited

U.S. PATENT DOCUMENTS

| | | | |
|---|---|---|---|
| 3,034,395 | 5/1962 | Zandman | 356/34 |
| 3,177,761 | 4/1965 | Redner | 356/366 |
| 3,885,875 | 5/1975 | Rosenfeld et al. | 356/369 |
| 4,158,506 | 6/1979 | Collett | 356/365 |
| 4,749,854 | 6/1988 | Martens | 250/225 |
| 4,801,798 | 1/1989 | Lange | 356/367 |
| 4,948,255 | 8/1990 | Watanabe | 356/367 |
| 4,973,163 | 11/1990 | Sakai et al. | 250/225 |

FOREIGN PATENT DOCUMENTS 0148942 6/1989 Japan .................................. 356/364

*Primary Examiner*—Hoa Q. Pham
*Attorney, Agent, or Firm*—Nikaido, Marmelstein, Murray & Oram

[57] ABSTRACT

A part for projecting a measuring light beam onto a sample and a light receiving part are arranged on the same side of a sample surface so that the measuring light beam is concentric with the light receiving part, the measuring light beam which is converted to a linearly polarized light beam through a polarizing element is projected to the sample so that the measuring light beam outgoing from the sample to the projecting side is received and detected through the same polarizing element. A plurality of sets of polarizing elements and light receiving parts are set so that the polarizing elements have different polarization directions, to calculate retardation from transmitted light intensity levels as obtained.

10 Claims, 5 Drawing Sheets

METHOD OF AND APPARATUS FOR MEASURING BIREFRINGENCE

BACKGROUND OF THE INVENTION

1. Field of the Invention

The present invention relates to a method of and an apparatus for measuring birefringence, and more particularly, it relates to a method of and an apparatus for measuring birefringence which is suitable for measuring retardation of a composite film, sheet, board or the like. The inventive method of and apparatus for measuring birefringence are particularly useful for measuring retardation and a principal refractive index direction of a liquid crystal phase contrast film, or a film or a sheet consisting of a composite material such as a polymer film which is laminated on a metal surface.

2. Description of the Background Art

In a conventional birefringence measuring apparatus, a photometric part is separated into a light projecting part and a light receiving part which are arranged on both sides of a sample surface respectively. Further, a polarizer and an analyzer which are employed as a set are arranged on the light projecting and light receiving parts respectively. Therefore, it takes much time and labor in order to adjust the polarizer and the analyzer in the same polarization direction in parallel nicol arrangement. This also applies to a case of adjusting the polarizer and the analyzer in relation of prescribed polarization directions such as vertical nicol arrangement.

Further, it is necessary to ensure a large space for installing the apparatus in a production line, since the apparatus is of a transmission type.

In addition, the apparatus is applicable only to light transmittable materials, since the same detects quantities of transmitted light.

Thus, the conventional birefringence measuring apparatus has problems in adjustment of the apparatus, the installation space and restriction of the sample to be measured.

SUMMARY OF THE INVENTION

In order to solve the aforementioned problems, an object of the present invention is to provide a method of and an apparatus for measuring birefringence with an excellent apparatus structure and a wide range of measurement.

In the method according to the present invention, a linearly polarized light beam is perpendicularly applied to a sample through a polarizing element, so that the linearly polarized light beam which is transmitted through the sample, reflected by a reflecting surface and again transmitted through the sample to outgo from the sample is again passed through the polarizing element forming the linearly polarized light to be detected.

The apparatus according to the present invention comprises a light source, light projecting optical means for converging light from the light source and applying the same to a surface of a sample as a parallel measuring light beam, a polarizing element which is arranged between the light projecting optical means and the sample for drawing linearly polarized light of a specific polarization direction, a sample part for receiving the sample or passing a travelling sample, and light detection means for detecting the measuring light beam, which is transmitted through the sample, reflected on a back side of the sample and again transmitted through the sample to exit from the surface of the sample, through the polarizing element.

In a preferred mode of the present invention, a photodetector provided in the light detection means is formed concentrically with a light path of the measuring light beam from the light projecting optical means.

In another preferred mode of the present invention, a plurality of sets of polarizing elements and light detection means are set in proximity to each other, so that optical axes of these sets are parallel to each other and polarization directions of the polarizing elements are different from each other.

In still another preferred mode of the present invention, a reflector is provided on a back side of the sample in the sample part, or a sample holder has a reflecting surface on a side for receiving the sample.

In a further preferred mode of the present invention, the light source, the light projecting optical means, the polarizing element and the light detection means are integrally formed as a photometric unit.

The apparatus according to the present invention further comprises means for detecting intensity levels of transmitted light with respect to at least three types of polarized light beams having different polarization directions respectively, means for sampling detection outputs of the detection means in accordance with prescribed programs, means for storing the sampled data, means for calculating retardation values and principal refractive index directions, and means for online-displaying angle distribution of intensity levels of reflected light.

Figure 1:
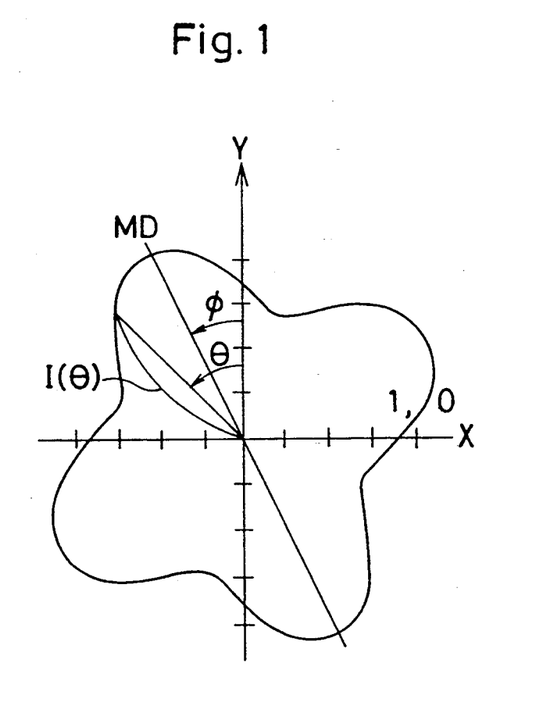
FIG. 1 illustrates dependence of intensity $I(\theta)$ of light transmitted through a polarizing element on angles of rotation of the polarizing element.

According to the present invention, intensity $I(\theta)$ of light transmitted through the polarizing element which is obtained when the polarizing element is rotated in place of a plurality of polarizing elements having different polarization directions which are arranged in proximity to each other is expressed as follows:

$$I(\theta) = A^2 \{1 + ((C-1)/2)\sin^2 2(\theta - \phi)\} \quad (1)$$

$$C \equiv \cos(2\pi R/\lambda) \quad (2)$$

where
- R = retardation of measured sheet
- A = amplitude of linearly polarized wave transmitted through polarizing element
- $\lambda$ = wavelength
- $\theta$ = angle of rotation of polarizing element with respect to a sample's reference direction
- $\phi$ = principal refractive index direction (MD direction) of measured sheet with respect to a sample's reference direction Assuming that X and Y represent axes of the measuring system, $I(\theta)$ is generally distributed as shown in FIG. 1.

In more concrete terms, description is now made on a procedure of arranging six polarizing elements having different polarization directions and obtaining retardation R and a principal refractive index direction $\phi$ from six measured values $I(\theta i)$ (i = 1, 2, ... 6) with respect to $\theta i$ by a numerical operation.

When both sides of the equation (1) are partially differentiated with A and C respectively, the following equations are obtained:

$$\partial I(\theta i)/\partial A = 2A\{1 + ((C-1)/2)\sin^2 2(\theta i - \phi)\} \quad (3)$$

$$\partial I(\theta i)/\partial C = (A^2/2)\sin^2 2(\theta i - \phi) \quad (4)$$

Consider the following functional determinant B:

$$B = \begin{bmatrix} \frac{\partial I(\theta 1)}{\partial A} & \frac{\partial I(\theta 1)}{\partial C} \\ \vdots & \vdots \\ \frac{\partial I(\theta n)}{\partial A} & \frac{\partial I(\theta n)}{\partial C} \end{bmatrix} \quad (5)$$

Proper initial values Ao and Co are supplied to:
P=(Ao, Co) to calculate the following expression with a residual determinant S:

$$e = -(B^t B)^{-1} B^t S$$

Then, similar calculation is carried out with a new initial value of P+e assuming that P=P+e, to repeat the calculation until convergence conditions are satisfied.

While the value of $\phi$ is also unknown in the equation (1), this value $\phi$ is regarded as a known value when the convergence values A and C are obtained by the aforementioned numerical operation. When the values A and C are calculated with first sampling values $I(\theta i)$ (i=1, 2, ... 6), the aforementioned calculation is carried out while varying the value of $\phi$ every degree from 0° to 90°, for example, to obtain the values A and C corresponding to the value $\phi$ every degree, and the optimum value for $\phi$ is a value $\phi_0$ which is obtained upon minimization of the sum of squares of remainders of the sampling values and calculated values. Thus obtained is the value $\phi_0$ to be regarded as the optimum value along the principal refractive index direction.

A value of R obtained by the equation (2) with a value of C corresponding to the optimum principal refractive index direction $\phi_0$ indicates the retardation of the measured sheet to be obtained.

When the values $\phi$ and R are obtained from second or later sampling values I(74 i), the range of $\phi$ is varied within a range of about ±5° around $\phi_0$ obtained from previous sampling values $I(\theta i)$ to obtain the values by a similar procedure, to reduce the calculation time and correctly obtain time changes of the values $\phi$ and R in film manufacturing steps.

According to the inventive birefringence measuring apparatus, the light outgoing from the sample on the surface receiving the measuring light beam is detected to measure birefringence, whereby a single polarizing plate can be applied to both of a polarizer and an analyzer in common and it is not necessary to adjust polarization directions of the polarizer and the analyzer dissimilarly to the prior art. Thus, it is possible to omit the time and labor for such adjustment.

Further, the polarizing plate serves both as the polarizer and as the analyzer absolutely in the same polarization direction, thereby improving measuring accuracy.

According to the present invention, the light projecting part and the light receiving part can be provided on one side of the sample to form a measuring head, whereby the measuring head can be reduced in size and no mechanism is required for synchronizing the light projecting part and the light receiving part for scanning the sample surface with the measuring head.

It is also possible to measure birefringence of a composite material comprising a metal plate which is covered with a polymer film or the like. it is also possible to measure these values in an online manner, whereby the present invention is also applicable to quality control in a production line. Further, it is also possible to measure birefringence of an ordinary single transparent film by providing a reflector for a measuring light beam on a back side of the sample, with no hindrance to the aforementioned measurement of a composite material.

The measuring light beam is reciprocally passed through the sample film, whereby a retardation value doubled as compared with that in general single passage is obtained from the detected value by calculation.

When light beams projected on the sample are arranged concentrically with photodetectors, it is not necessary to employ a half mirror or the like.

According to the present invention, it is also possible to measure temperature characteristics of the retardation value by heating or cooling the sample. Heating means such as a hot plate or cooling means may be provided on a back surface of a sample when the sample consists of a composite material comprising a metal plate which is covered with a polymer film, while such means may be provided on a back surface of a sample through a reflector when the sample consists of a light transmittable film or sheet.

According to the present invention, further, it is also possible to measure retardation of a wall surface of a resin container or a cylinder. In this case, a reflecting film may be formed on an inner surface of the container or the cylinder by silver mirror reaction or chemical plating, to apply a measuring light beam from outside the container or the cylinder and receive reflected light.

Retardation etc. can be measured also on a curved sample surface, with a large effect particularly in measurement of anisotropy of a polymer film which is laminated on a surface of a metal pipe or the like.

The foregoing and other objects, features, aspects and advantages of the present invention will become more apparent from the following detailed description of the present invention when taken in conjunction with the accompanying drawings.

DESCRIPTION OF THE PREFERRED EMBODIMENTS

Figure 2:
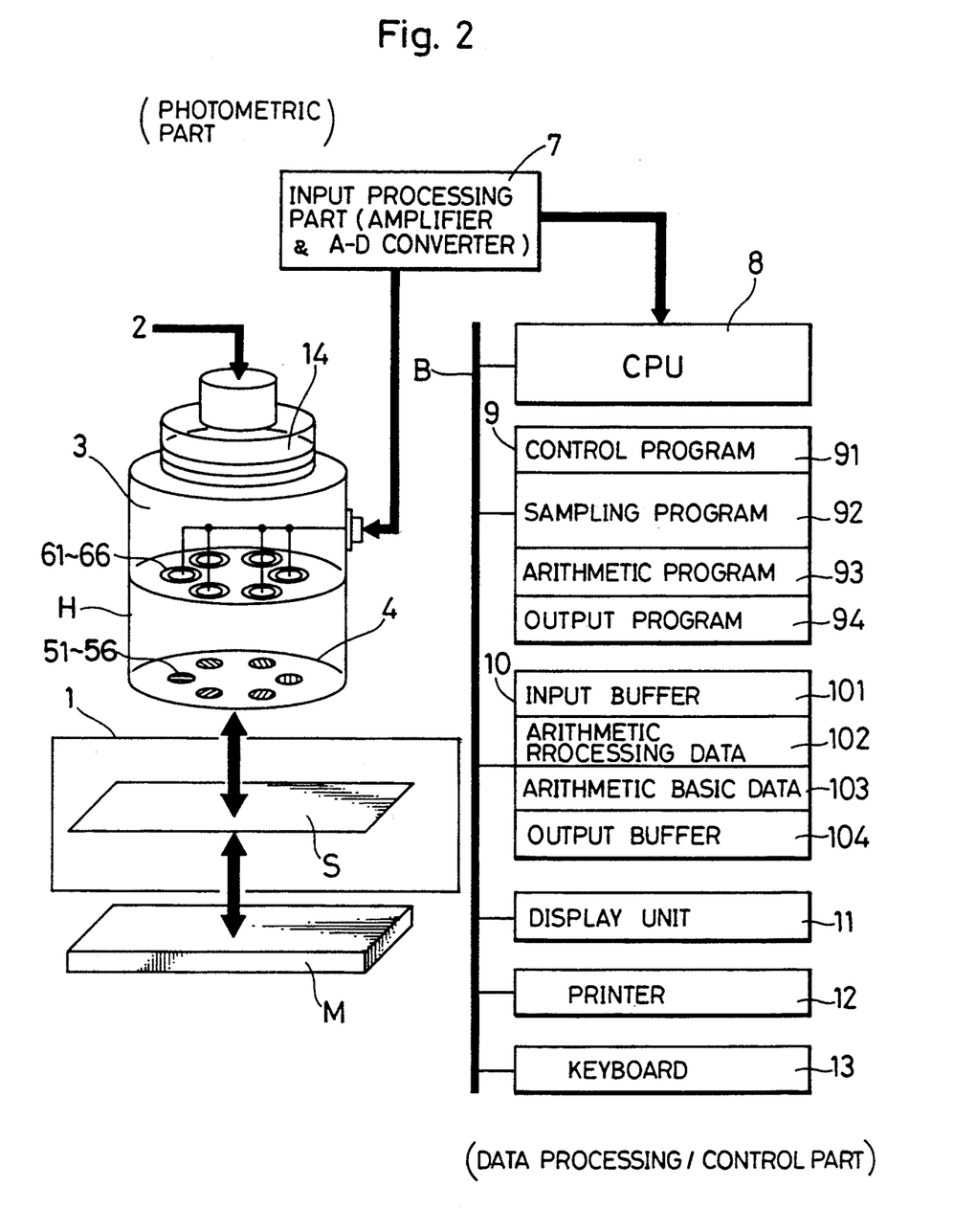
FIG. 2 is a schematic block diagram showing an apparatus according to an embodiment of the present invention.

FIG. 2 is a schematic block diagram showing a retardation measuring apparatus according to an embodiment of the present invention. A sample part 1 has a sample holder, which receives a sample S to be measured thereon. A measuring head H is arranged above the sample part 1. In order to measure two-dimensional distribution of birefringence and other optical properties, a mechanism may be provided for driving one or both of the sample holder and the measuring head H for relatively carrying out two-dimensional scanning between the same. In the case of a travelling sample, the measuring head H may be one-dimensionally driven in a direction perpendicular to the travelling direction.

A light reflector M is arranged on a back side of the sample S set in the sample part 1, i.e., a side which is opposite to a measuring light beam projected on the sample S, in parallel with the sample S relatively in proximity thereto. Thus, it is possible to cope with both of an ordinary transmittable sample and a sample comprising a metal plate which is covered with a transparent sample. Namely, (A) In order to measure a transmittable sample, the measuring light beam which is transmitted through the sample is reflected by the reflector M and again oppositely transmitted through the sample, to outgo toward the light projecting side.

Figure 3A:
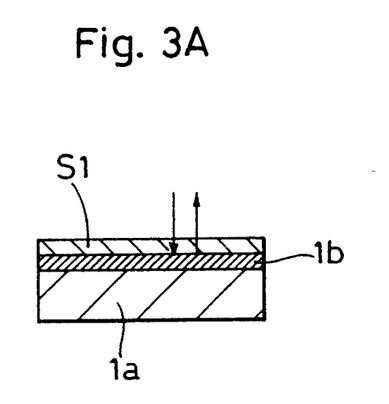
FIG. 3A is a sectional view showing an exemplary sample part in the apparatus according to the embodiment of the present invention.

When a stationary sample is stopped on the sample holder for measurement of one point, or one or both of the sample holder and the measuring head are moved to measure distribution in a certain two-dimensional range, it is possible to enlarge the range of measurement by providing a mirror finished surface layer 1b on a sample holder 1a as shown in FIG. 3A, for example. In order to provide the mirror finished surface layer 1b on the sample holder 1a, the surface of the sample holder 1a may be worked to be directly provided with a mirror finished surface, the surface may be treated by silver deposition or the like to have a mirror finished surface, or provided with a reflecting mirror which is laminated on its surface. In the case of measuring an ordinary transmittable sample S1, light which is transmitted through the sample S1 is reflected by the mirror finished surface layer 1b and again transmitted through the sample S1, to exit toward the light projecting side in parallel with the incident light beam.

Figure 3B:
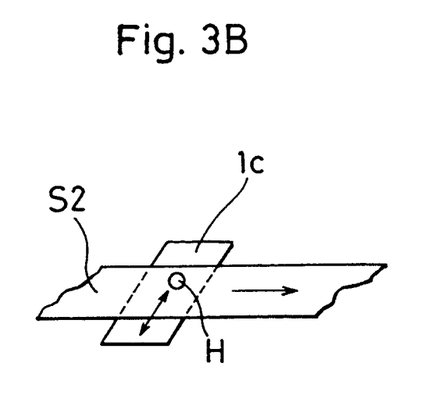
FIG. 3B is a sectional view showing another exemplary sample part in the apparatus according to the embodiment of the present invention.

In order to measure a transmittable sample S2 of a wide travelling sheet, on the other hand, a longitudinal reflector 1c is arranged on the back side of the sample S2 to cover the overall width thereof as shown in FIG. 3B, to facilitate measurement of two-dimensional distribution. Assuming that X represents the sample travelling direction, the two-dimensional distribution can be measured by reciprocating the measuring head H along a direction Y which is perpendicular thereto, whereby the two-dimensional distribution along the overall width and the overall length of the travelling sample S2 can be covered by the longitudinal reflector 1c shown in FIG. 3B.

Figure 4:
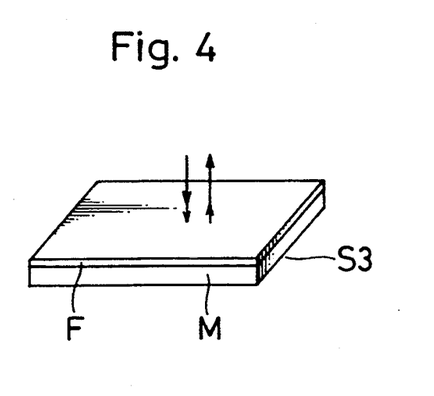
FIG. 4 is a perspective view showing still another exemplary sample part in the apparatus according to the embodiment of the present invention.

(B) In the case of measuring a sample S3 of a composite material comprising a reflective material M of a metal or the like which is covered with a transparent film F as shown in FIG. 4, a beam which is incident upon this sample S3 is reflected by the surface of the reflective material M and again transmitted through the transparent film F to exit toward the projecting side. Thus, the measurement is not hindered even if a reflector of the sample holder is present on the back side of the sample S3.

Referring again to FIG. 2, a light source part 2 emits light, which is transmitted to a convergent optical system 3 through an optical fiber bundle or the like. The convergent optical system 3 is formed to be capable of supplying a plurality of parallel light beams in a number required for measurement, or a parallel light beam having a sufficiently large section capable of including these light beams, by a condensing lens or a concave mirror included therein.

A filter part 14, which can select and pass light of a required specific wavelength, has a mechanism for switching selected wavelengths. The filter part 14 can be set on a light path between the light source 2 and the sample part 1, a light path between the sample S and a detection part, or another position such as that immediately in front of photodetectors 61 to 66 of a light receiving unit 4 as described later.

Figure 5:
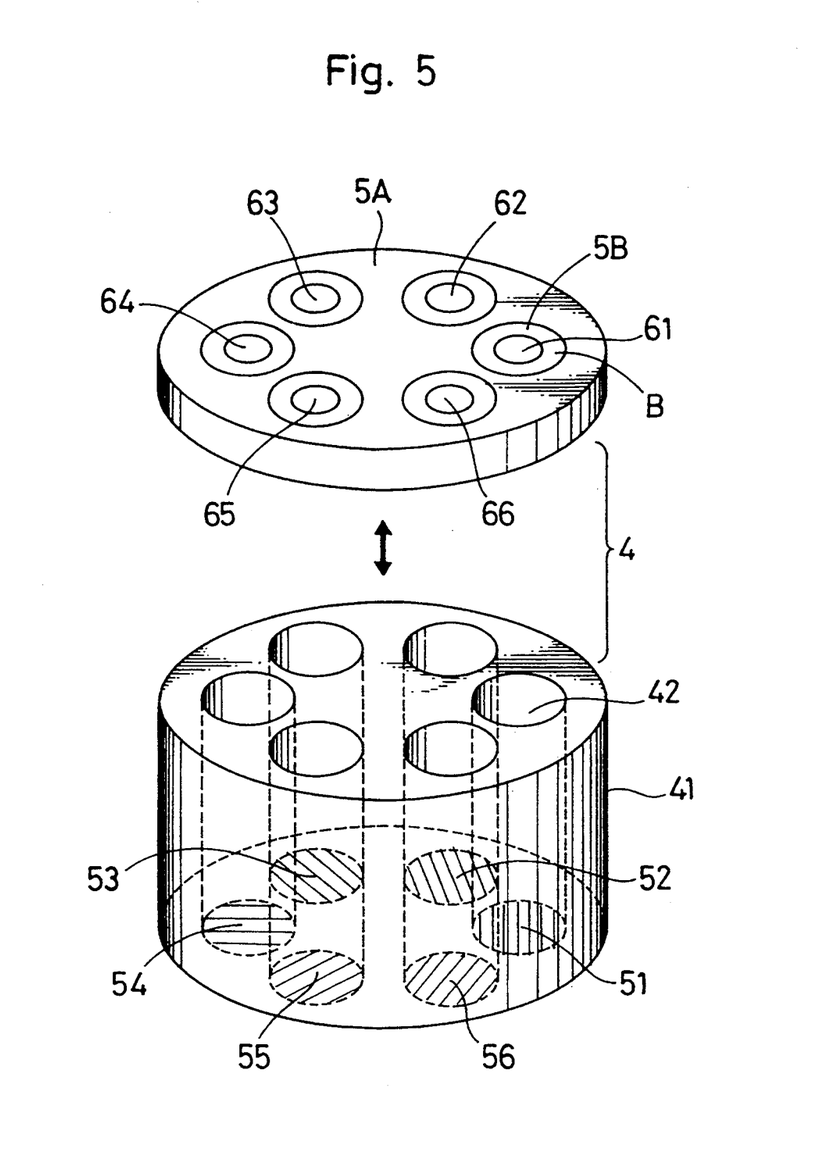
FIG. 5 is a perspective view showing an exemplary light receiving unit in the apparatus according to the embodiment shown in FIG. 2.
Figure 6:
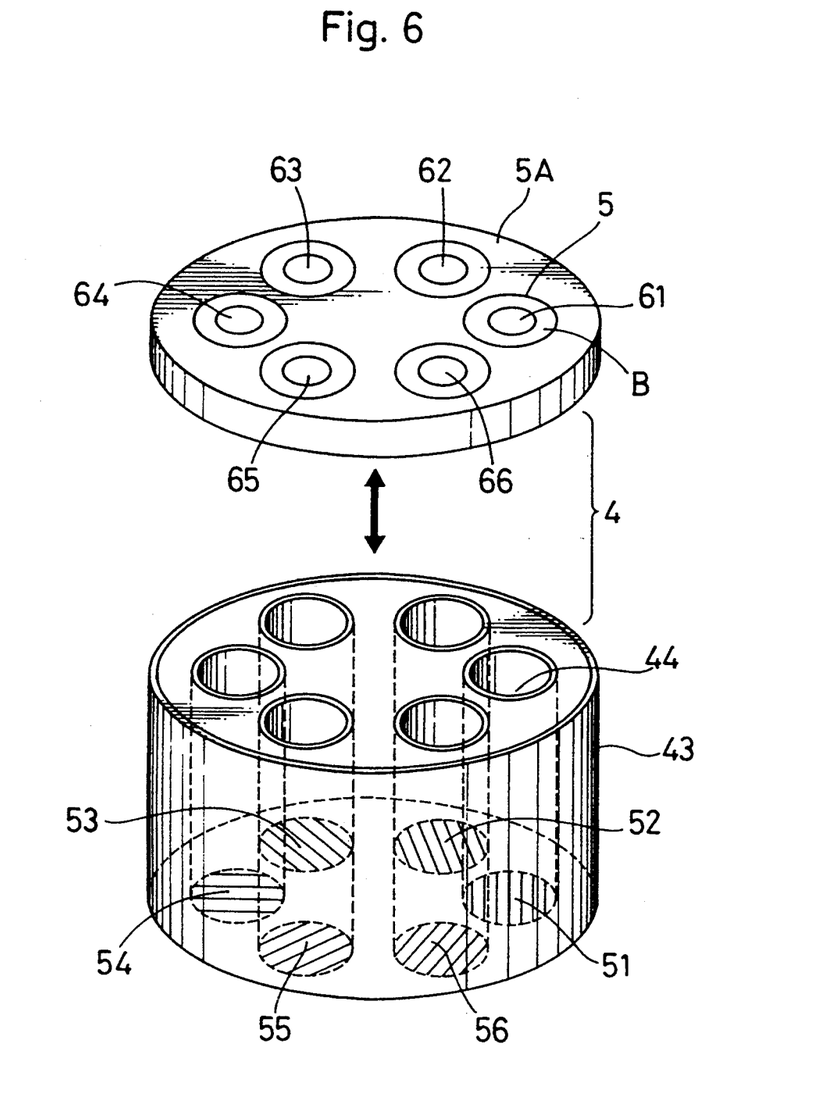
FIG. 6 is a perspective view showing another exemplary light receiving unit in the apparatus according to the embodiment shown in FIG. 2.

FIGS. 5 and 6 illustrate concrete examples of the light receiving unit 4 respectively. Referring to FIG. 5, the light receiving unit 4 is formed by a cylindrical body block 41 having a plurality of measuring light paths 42 formed by circular holes which are parallel to the axis of the cylindrical body block 41 and provided on the circumference of the cylindrical body block 41 about its axis. While the number of the measuring light paths 42 is not restricted, FIG. 5 shows six as an example. The cylindrical block 41 is preferably made of an opaque material, in order to prevent incidence of interfering light.

The measuring light paths 42 are not restricted to the aforementioned arrangement on the circumference, but may be arranged in alignment along a direction X or Y, two-dimensionally arranged along the directions X and Y, arranged on respective ones of a plurality of concentric circumferences as well as on a center, or arranged at random or in other mode. Further, it is possible to select specific ones of a plurality of measuring channels which are arranged in a set in response to sample characteristics or an object of measurement, such as those on a line in the direction X or Y or those at the center of a circle and on the innermost circumference in particular to obtain birefringence from the data.

Circular polarizing plates 51 to 56 are fixed at lower ends of the measuring light paths 42 respectively. Polarization directions of the polarization plates 51 to 56 are displaced at proper angles, such as 30° in FIG. 5, for example, from each other. Assuming that the polarizing plate 51 is in a polarization direction of 0°, the polarizing plates 52 and 53 are displaced counterclockwise by +30° and +60° respectively, for example.

Each of the polarizing plates 51 to 56 serves both as a polarizer and an analyzer for light which is projected on the sample S and for a light receiving part receiving the light outgoing from the sample S respectively, to attain action equivalent to those of two polarizing plates which are arranged in a parallel nicol state.

A photodetector holding plate 5A which is identical in diameter to the body block 41 is formed by a transparent or opaque disk having the same diameter as the body block 41, for example, to be provided with the photodetectors 61 to 66 having slightly smaller diameters than the measuring light paths 42 in positions corresponding thereto in a coaxial manner, while downwardly directing light receiving surfaces in FIG. 5. The photodetectors 61 to 66 may be held on the front or back side of the holding plate 5A, or embedded therein.

These photodetectors 61 to 66 can be directly provided on the holding plate 5A, which is made of a transparent material in this case. The photodetectors 61 to 66 are mounted on centers of transparent photodetector mounting plates 5B, for facilitating adjustment of positions for mounting the photodetectors 61 to 66 and replacement thereof, which in turn are fixed on prescribed positions of the holding plate 5A by bonding or adhesion.

When the holding plate 5A is made of an opaque material, on the other hand, circular holes which are substantially identical in diameter to the measuring light paths 42 may be provided on respective positions of the holding plate 5A corresponding to the measuring light paths 42 so that transparent mounting plates having the same diameters as the holes are engaged in these circular holes or those having larger diameters than the circular holes are fixed to required positions of the holding plate 5A as described above.

In either case, the photodetectors 61 to 66 correspond to centers of the measuring light paths 42, so that light transmitting portions are formed in concentric annular portions B around the photodetectors 61 to 66.

Alternatively, light transmitting portions may be defined in central portions of light paths corresponding to the measuring light paths 42 so that the photodetectors 61 to 66 can be arranged in an annular manner, as the case may be.

The photodetector holding plate 5A, which is shown in separation from the body block 41 in FIG. 5, is fixed to an upper portion of the body block 41 through screws or a method of bonding, adhesion or the like so that the axes of corresponding ones of the polarizing plates 51 to 56, the measuring light paths 42 and the photodetectors 61 to 66 are aligned with each other.

Such concentric arrangement may not be particularly strict but slight displacement between the centers and that from circular arrangement are allowable.

The photodetectors 61 to 66 are prepared from photoelectric conversion elements such as solar cells, photodiodes or CCD elements. These may serve as independent detectors for the respective optical axis positions, while a sufficiently large CCD two-dimensional sensor covering all optical axes may be employed to successively read data by a program every range corresponding to each optical axis.

Detection outputs from the photodetectors 61 to 66 are incorporated in a data processing part through an input processing part 7 described later.

FIG. 6 shows another exemplary light receiving unit 4. A cylindrical box member 43 having a bottom surface is provided with a plurality of (six in FIG. 6) small cylinders 44 having the same shapes and the same sizes, which are arranged in parallel about the cylindrical axis of the box member 43. The overall bottom portion or portions corresponding to measuring light paths of the cylindrical box member 43 are formed by transparent materials, while its side surface is preferably opaque.

Further, side surfaces of the small cylinders 44 are preferably made of opaque materials, in order to prevent interference between the respective measuring light paths and interference with external light.

Polarizing plates 51 to 56 may be arranged on the bottom surface of the cylindrical box member 43, or the small cylinders 44 may be provided with transparent bottom surfaces for arranging the polarizing plates 51 to 56.

Arrangement and structures of photodetectors 61 to 66, positions in planar arrangement of the measuring light paths and the structures and positions in planar arrangement of the polarizing plates 51 to 56 appearing in FIG. 6 are identical to those in FIG. 5.

Referring again to FIG. 2, a plural light beam measuring photometric part including the light source 2, the convergent optical system 3, the light receiving unit 4 and the filter part 14, which is present on the same side with respect to the sample surface, can be unified as a single measuring head H. Thus, the photometric part can be extremely reduced in size and a scanning mechanism for the measuring head H can be implemented in a simple structure for measurement of two-dimensional distribution or the like, to be extremely effectively applied to measurement of two-dimensional distribution of birefringence or the like.

The following part is the data processing part, whose main portion can be set in a position which is separated from the job site independently of the photometric part. In this case, measured data, control commands and the like are transmitted to the photometric part through wire or wireless electrical communication means, or means such as optical communication using an optical fiber.

The input signal processing part 7 amplifies and A-D- (analogue to digital) converts respective detection outputs from the photodetectors 61 to 66, for introducing the same into the data processing part. Elements and a transmission part of the input signal processing part 7 may be properly provided in the same position as the photometric part, in response to the system structure of the overall measuring apparatus.

Symbol B denotes a data bus line of a processing/control part, and numeral 8 denotes a CPU. A program storage part 9 which is formed by a fixed or semi-fixed memory such as a ROM or EPROM stores various types of control/arithmetic programs. A storage region 91 for a control program for controlling the operation of the overall apparatus may comprise a program for maintenance work or the like, in addition to the program for the overall control. Another storage region 92 stores a sampling program for instructing sampling of data from the detection outputs, still another storage region 93 stores an arithmetic program for carrying out various types of required arithmetic operations from measured data stored in a memory 10 described later, and a further storage region 94 stores an output program for outputting processed data to a CRT 11, a printer 12 and the like.

The aforementioned sampling program can properly select a system of sampling data every prescribed distance of movement or prescribed time of a sample, which is in the form of a continuous sheet, discharged from a production line, so that the detection outputs from the photodetectors 61 to 66 are sampled in the input processing part 7 and stored in the memory 10 with information on numbers (polarization directions) of the photodetectors 61 to 66 in accordance with the selected sampling program.

The aforementioned arithmetic program is adapted to carry out various types of required arithmetic operations including retardation calculation from basic data stored in the memory 10 and the measured data.

The output program is adapted to process overall output control such as CRT display of the results of measurement, document printing etc., while it is also possible to display an angle distribution diagram of transmission intensity of the polarized light every time a photodetector output is sampled and stored in the memory 10 for continuously displaying changes of birefringence in the direction of flow of the measured sheet in an online system.

The memory 10, which is formed by a RAM having a variable storage content, for example, has an input buffer memory 101 for temporarily storing the aforementioned measured data introduced from the input processing part 7, an arithmetic processing data storage region 102 for storing processed data etc., an arithmetic basic data storage region 103 storing basic data required for data processing, numerical expressions etc., and an output buffer memory 104 storing data for CRT display and a hard copy.

A display unit 11 is formed by a CRT or a liquid crystal display unit, for example. This display unit 11 may be provided with several display surfaces, for monitor, total display of the results of measurement and online display of a specific result of measurement. Numeral 12 denotes a printer, and numeral 13 denotes a keyboard input unit.

The operation of the inventive apparatus is now schematically described with reference to FIG. 2. The light emitted from the light source 2 is converged by the convergent optical system 3 into a parallel beam, which is passed through the photodetector mounting plate 5B provided around the photodetectors 61 to 66, converted to monochromatic light components through the filter part 14 in proper positions, and passed through the polarizing elements 51 to 56 to enter the sample part 1 as polarized measuring light beams of respective polarization directions. The measuring light beams are transmitted through corresponding transparent film positions of the sample S, reflected by the reflecting surface provided on the back side, again transmitted through the transparent film portions to exit from the sample S, and again passed through the polarizing elements 51 to 56, to be received and detected by the corresponding photodetectors 61 to 66 of the light receiving unit 4.

The detection outputs of the photodetectors 61 to 66 are read along the sampling program stored in the storage region 92, A–D converted and stored in the input buffer memory 101, so that principal refractive index directions and retardation values are calculated by the arithmetic program stored in the storage region 93.

The arithmetic operation results are displayed on the display unit 11 by the output program stored in the storage region 94 at any time and printed by the printer 12, while a specific result of measurement is online-displayed simultaneously with measurement.

EXPERIMENTAL EXAMPLE

The inventive apparatus (see FIGS. 2 and 5) was employed to measure retardation and orientation angles of a polymer film sample. The results of measurement were compared with those of transmitted light measurement in a conventional system, as shown in Tables 1 and 2. Since measuring light beams were reciprocally passed through the polymer film sample in the inventive system, $\frac{1}{2}$ of the measured retardation values were compared with values measured by the conventional system.

(TABLE 1)

| Sample: PET (polyethylene terephthalate) (Thickness = 12 μm) | | | |
|---|---|---|---|
| | ① Reflection type | ① Conventional type | ①/②-② |
| $\phi(°)$ | −41 | −41 | — |
| R (nm) | 549.7 | 276.8 | −1.95 |

(TABLE 2)

| Sample: PP (polypropylene) Thickness = 30 μm) | | | |
|---|---|---|---|
| | ① Reflection type | ① Conventional type | ①/②-② |
| $\phi(°)$ | 2 | 0 | — |
| R (nm) | 98.2 | 52.1 | −3.0 |

Table 1 shows the results of measurement of polyethylene terephthalate films having thicknesses of 12 μm. $\phi$ denotes principal refraction index direction and R denotes retardation. Remarkably excellent coincidence was attained in both of the retardation and the principal refractive index directions (orientations). On the other hand, Table 2 shows the results of measurement of polypropylene films having thicknesses of 30 μm. Although deviation of several % is recognized, the same was sufficiently practical.

According to the present invention, the aforementioned measurement of birefringence etc. is applicable to both of a transparent film and a composite film comprising a reflective surface of a metal or the like which is covered with a polymer film or the like, while it is possible to attain various effects such as simplification of the apparatus structure, improvement in efficiency of an adjusting operation and the like.

According to the present invention, further, it is possible to reduce the measuring head in size by unifying the light transmission system and the photodetectors as shown in FIG. 2, no employment of a half mirror etc. is required, and it is possible to obtain remarkably excellent results of measurement.

While the above description is made with reference to measurement of birefringence particularly in relation to an online measuring apparatus, the present invention is also applicable to a case of relatively rotating polarizing elements with respect to a sample for measuring birefringence from angle distribution of beams transmitted through polarizers, the sample and analyzers (formed by the polarizing elements similarly to the polarizers). Further, the optical system according to the present invention is not restricted to measurement of birefringence, but is also applicable to measurement of other optical properties such as light transmission, reflection, refraction, polarization and the like.

In summary, the present invention has the following effects:

(1) A single polarizing plate can serve both as a polarizer and an analyzer, whereby absolutely no deviation of polarization directions is caused in adjustment and measurement accuracy can be improved.

(2) It is possible to measure retardation and a principal refractive index of a film, a sheet or the like which is laminated to a metal surface or the like. Further, it is also possible to measure these values in an online manner, whereby the present invention is also applicable to quality control in a production line.

(3) The apparatus body can be reduced in size, whereby the installation space can be easily ensured.

(4) Retardation etc. can be measured also on a curved sample surface, with a large effect particularly in measurement of anisotropy of a polymer film which is laminated on a surface of a metal pipe, a polymer tube, a polymer container or the like.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. A method of measuring birefringence including both of a principal refractive index direction and a retardation by perpendicularly applying a plurality of linearly polarized light beams to a sample through each of a plurality of polarizing elements provided in proximity to each other and different from each other in polarization direction, again passing said linearly polarized light beams, being transmitted through said sample, reflected by a reflecting surface and again transmitted through said sample to exit said sample, through each of said polarizing elements forming each of said linearly polarized light beams, and detecting said linearly polarized light beams passing through each of said polarizing elements.

2. An apparatus for measuring birefringence including both of a principal refractive index direction and a retardation, comprising:
    a light projecting optical means for projecting a plurality of parallel measuring light beams to a surface of a sample;
    a plurality of polarizing elements disposed between said light projecting optical means and said sample, said polarizing elements being provided in proximity to each other and different from each other in polarization direction for selecting linearly polarized light of specific polarization directions, respectively;
    a sample supporting part for supporting said sample; and
    a plurality of light detection means each of which forms a pair with each of said polarizing elements for detecting said measuring light beams, each of said measuring light beams being transmitted through said sample, reflected back towards the incident surface of said sample and again transmitted through said sample to enter said respective light detection means through said respective polarizing elements.

3. An apparatus for measuring birefringence in accordance with claim 2, further comprising means for sampling transmitted light intensity levels with respect to a plurality of measuring light beams, said plurality of measuring light beams comprising polarized light beams having different polarization directions from said light detection means in accordance with a prescribed program, said apparatus further comprising means for storing sampled data, means for calculating retardation values and principal refractive index directions from said sampled data, and means for online-displaying angle distribution of reflected light intensity levels.

4. An apparatus for measuring birefringence in accordance with claim 3, wherein
    said means for calculating said retardation values and said principal refractive index directions utilizes sampled data of transmitted light intensity values $I(\theta i)$ obtained through respective said polarizing elements having different polarization directions for obtaining said retardation values and said principal refractive index directions through:
    a step 1 of obtaining values A and C for minimizing the sum of squares of remainders of calculated and sampled values of said polarizing element transmitted light intensity values $I(\theta i)$ with known $\phi$, $$I(\theta i) = A^2 \{1 + ((C-1)/2)\sin^2 2(\theta i - \phi)\}$$

where
    C: $\cos(2\pi/R/\lambda)$
    R: retardation of sample
    A: amplitude of linearly polarized wave transmitted through polarizing element
    $\lambda$: wavelength
    $\theta i$: angle of rotation of each polarizing element with respect to a sample's reference direction
    $\phi$: principal refractive index direction (MD direction) of sample with respect to a reference direction of the sample
    i: number of polarizing element,
    a step 2 of varying $\phi$ from 0° to 90° for obtaining a value $\phi_0$ minimizing the sum of squares of remainders of said sampled values and calculated values, and
    a step 3 of obtaining retardation R of said measured sheet through a value C with respect to an optimum principal refractive index direction $\phi_0$ as obtained.

5. An apparatus for measuring birefringence in accordance with claim 4, wherein
    a range for varying $\phi$ is restricted in a narrow range with respect to the previously obtained value of $\phi_0$ in second or later measurement, to carry out a similar operation.

6. An apparatus for measuring birefringence in accordance with claim 2, wherein
    said sample part has a sample holder being provided with a reflecting surface on a sample side.

7. An apparatus for measuring birefringence in accordance with claim 2,
    wherein said light projecting optical means, polarizing elements and plurality of light detection means are assembled integrally to form a photometric unit.

8. An apparatus for measuring birefringence in accordance with claim 7, wherein
    a photodetector of said light detection means is formed to be concentric with a light path of said light projecting optical means for said measuring light beam,
    a plurality of pairs of said polarizing elements and said light detection means being provided in proximity to each other, said plurality of pairs being so arranged that optical axes thereof are in parallel with each other and polarization directions of said polarizing elements are different from each other.

9. An apparatus for measuring birefringence in accordance with claim 7, wherein
    a cylindrical body block is provided with several measuring light paths formed by circular holes being parallel to an axis of said cylindrical body block on a circumference about said axis of said cylindrical body block, said polarizing elements, being so sized as to block said measuring light paths, being mounted one by one on respective ends of said measuring light paths being closer to said sample, wherein said plurality of light detection means comprising photodetectors being smaller in diameter than said measuring light paths being mounted on respective other ends of said measuring light paths in a concentric manner while directing light receiving surfaces toward said polarizing elements.

10. An apparatus for measuring birefringence, comprising:

a light source;

a light projecting optical means coupled to said light source for applying light from said light source to a surface of a sample as a parallel measuring light beam;

a polarizing element disposed between said light projecting optical means and said sample for selecting linearly polarized light of a specific polarization direction;

a sample supporting part for receiving and supporting said sample; and a light detection means for detecting said measuring light beam, said measuring light beam being transmitted through said sample, reflected back towards said sample and again transmitted through said sample to exit said surface of said sample, through said polarizing element;

wherein a photodetector of said light detection means is formed to be concentric with a light path of said light projecting optical means for said measuring light beam.

* * * * *